United States Patent [19]
Shimizu et al.

[11] Patent Number: 5,567,350
[45] Date of Patent: Oct. 22, 1996

[54] SILACYCLOHEXANE COMPOUND, A METHOD OF PREPARING IT AND A LIQUID CYRSTAL COMPOSITION CONTAINING IT

[75] Inventors: Takaaki Shimizu; Takeshi Kinsho; Tsutomu Ogihara; Tatsushi Kaneko; Ryuichi Saito, all of Kubiki-Mura; Hideshi Kurihara, Kawasaki, all of Japan

[73] Assignee: Shin-Etsu Chemical Co., Ltd., Tokyo, Japan

[21] Appl. No.: 383,368

[22] Filed: Feb. 3, 1995

[30] Foreign Application Priority Data

Feb. 4, 1994 [JP] Japan ..................... 6-033156

[51] Int. Cl.$^6$ ............ C09K 19/34; C09K 19/30; C07F 7/08; G02F 1/13
[52] U.S. Cl. ............... 252/299.61; 252/299.63; 556/406
[58] Field of Search ............ 556/406; 252/299.63, 252/299.61

[56] References Cited

U.S. PATENT DOCUMENTS

| | | | |
|---|---|---|---|
| 2,607,791 | 8/1952 | Goodwin et al. | 556/406 X |
| 2,872,471 | 2/1959 | Ramsden et al. | 556/406 X |
| 5,302,734 | 4/1994 | Jung et al. | 556/406 |
| 5,454,977 | 10/1995 | Shimizu et al. | 252/299.61 |

FOREIGN PATENT DOCUMENTS

| | | |
|---|---|---|
| 0355008 | 8/1989 | European Pat. Off. . |
| 0632044 | 6/1994 | European Pat. Off. . |
| 0630903 | 6/1994 | European Pat. Off. . |

*Primary Examiner*—C. H. Kelly
*Attorney, Agent, or Firm*—Townsend & Banta

[57] ABSTRACT

A silacyclohexane compound of formula (I):

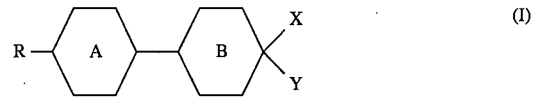

wherein R denotes a linear-chain alkyl group, a mono- or di-fluoroalkyl group, a branched-chain alkyl group, an alkoxyalkyl group, or an alkenyl group: at least one of

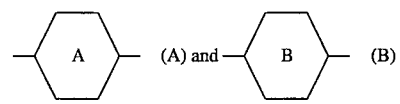

denotes a 1-sila-1,4-cyclohexylene or a 4-sila-1,4-cyclohexylene group whose silicon at position 1 or 4 is H, F, Cl or $CH_3$, and the other denotes a 1,4-cyclohexylene group, a 1-sila-1,4-cyclohexylene or a 4-sila-1,4-cyclohexylene group whose silicon at position 1 or 4 is H F, Cl or $CH_3$; X denotes a substitutional group at an equatorial position, specifically CN, an alkyl group with its end group replaced by a trifluoromethyl group, an alkoxy group, an alkanoyloxy group, an alkoxycarbonyl group, a linear-chain alkyl group, or an alkoxyalkyl group; Y denotes a group at an axial position, specifically H or CN when Y is connected to a carbon atom in said (B) group or H, F, Cl or $CH_3$ when Y is connected to a silicon atom in said (B) group.

6 Claims, No Drawings

SILACYCLOHEXANE COMPOUND, A METHOD OF PREPARING IT AND A LIQUID CYRSTAL COMPOSITION CONTAINING IT

BACKGROUND OF THE INVENTION

1. Field of the Invention

This invention relates to a new silacyclohexane compound, a method of preparing it, and a liquid crystal composition which contains it, as well as a liquid crystal display element containing said liquid crystal composition.

2. The Prior Art

A liquid crystal display element utilizes the optical anisotropy and dielectric anisotropy of liquid crystal substances. Display methods include the TN mode (twisted nematic mode), the STN, mode (super twisted nematic mode), the SBE mode (super birefringence mode), the DS mode (dynamic scattering mode), the guest-host mode, the DAP mode ("deformation of aligned phase" mode) and the OMI mode (optical mode interference mode). The most common display device has a twisted nematic structure based on the Schadt-Helfrich mode.

The properties required of the liquid crystal substance used in these liquid crystal displays are somewhat different depending on the display method. However, a wide liquid crystal temperature range and stability with regard to moisture, air, light, heat, electric fields, etc., are properties commonly required by all display methods. Furthermore, it is desirable for the liquid crystal material to have a low viscosity, and also to have a short address time, low threshold voltage and high contrast in the cell(s).

Currently, there is no single compound which satisfies all these requirements. In practice, liquid crystal mixtures are used which are obtained by mixing several to more than ten liquid crystal compounds and latent liquid crystal compounds. Because of this, it is also important that the components of a liquid crystal composition mix easily.

Among liquid crystal compounds which can be these components, one of the components conventionally known which has a medium positive dielectric anisotropy and a small anisotropy of the refractive index Δn is a compound which has the bicyclohexyl ring structure such as represented by the general formula shown below.

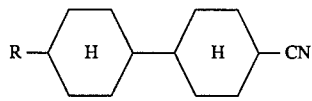

(Japanese published patent Tokko Sho 59-4420)

Also, the compounds with the bicyclohexyl ring structure represented by the general formulas shown below are known to have near zero dielectric anisotropy while their Δn is small and their viscosity is low.

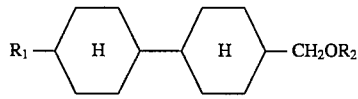

(Tokko Sho 62-15052)

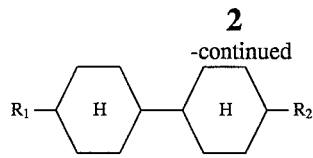

(Tokko Sho 63-10137)

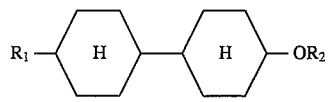

(Tokko Hei 5-20418)

In recent years, along with the expansion of the applications of liquid crystal displays, the characteristics required of liquid crystal materials are becoming more and more advanced and demanding. In particular, superior characteristics such as a faster response time and a wider angle of visibility are increasingly in demand.

In order to shorten the response time, it is necessary to lower the viscosity of the liquid crystal composition. To widen the angle of visibility, it is required to have an optimum first minimum of the retardation, i.e. to reduce the anisotropy of the refraction index.

BRIEF SUMMARY OF THE INVENTION

From such a viewpoint, the object of this invention is to provide a liquid crystal compound containing a silacyclohexane ring(s) with a silicon(s) atom in its molecular structure, characterized by having an effect of reducing the anisotropy of the refractive index and the viscosity when used as a component of a liquid crystal composition as well as being completely different from the conventional liquid crystal compounds with the bicyclohexyl ring structure.

That is, this invention is a silacyclohexane compound represented by the following general formula (I).

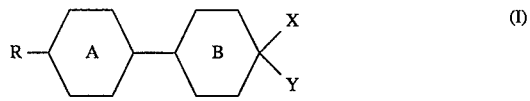

In this formula, R denotes a linear-chain alkyl group with a carbon number of 1–10, a mono- or di-fluoroalkyl group with a carbon number of 1–10, a branched-chain alkyl group with a carbon number of 3–8, an alkoxyalkyl group with a carbon number of 2–7, or an alkenyl group with a carbon number of 2–8.

At least one of

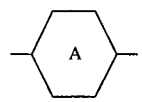 (A)

and

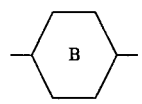 (B)

denotes a 1-sila-1,4-cyclohexylene or a 4-sila-1,4-cyclohexylene group whose silicon at position 1 or position 4 has a substitutional group(s) of H, F, Cl or $CH_3$ and the other denotes a 1,4-cyclohexylene group, a 1-sila-1,4-cyclohexylene or a 4-sila-1,4-cyclohexylene group whose silicon at position 1 or position 4 has a substitutional group of H, F, Cl, or CH₃. X denotes a substitutional group at an equatorial position, specifically CN, an alkyl group with a carbon number of 1–10 and with its end group replaced by a trifluoromethyl group, an alkoxy group with a carbon number of 1–10, an alkanoyloxy group with a carbon number of 2–10, an alkoxycarbonyl group with a carbon number of 1–10 or a linear-chain alkyl group with a carbon number of 1–10, or an alkoxyalkyl group with a carbon number of 2–7. Y denotes a substitutional group at an axial position, specifically H or CN when Y is connected to a carbon atom in said group (B) group, or H, F, Cl or CH₃ when Y is connected to a silicon atom in said (B) group, or H, F, Cl or CH₃ when Y is connected to a silicon atom in said (B) group, and the relationship between R and (B) as well as between (A) and the substitutional group X is trans.

This invention is also a method of preparing the silacyclohexane compound as represented by said general formula (I) characterized by the use of a carbon-carbon bond formation reaction or a carbon-silicon bond formation reaction between an organometallic reagent

R—M (M denotes MgP (P denotes a halogen atom), ZnP or Li) and

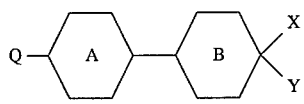

(Q denotes a halogen atom, or an alkoxy, methanesulfonyl, benzenesulfonyl or p-toluenesulfonyl group).

This invention is also a method of preparing the silacyclohexane compound as represented by said general formula (I) characterized by the use of a carbon-carbon bond formation reaction or a carbon-silicon bond formation reaction between an organometallic reagent

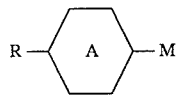

and

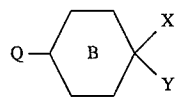

This invention is also a method of preparing the silacyclohexane compound as represented by said general formula (I) characterized by the use of a carbon-carbon bond formation reaction or a carbon-silicon bond formation reaction between an organometallic reagent

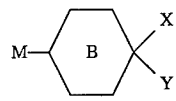

and

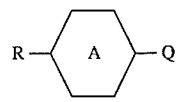

Furthermore, this invention is a liquid crystal composition comprising the compound as represented by the general formula (I) and a liquid crystal display element characterized by containing this liquid crystal composition.

DETAILED DESCRIPTION

The new compounds represented by said general formula (I) are silacyclohexane compounds specifically represented by ring structures shown below:

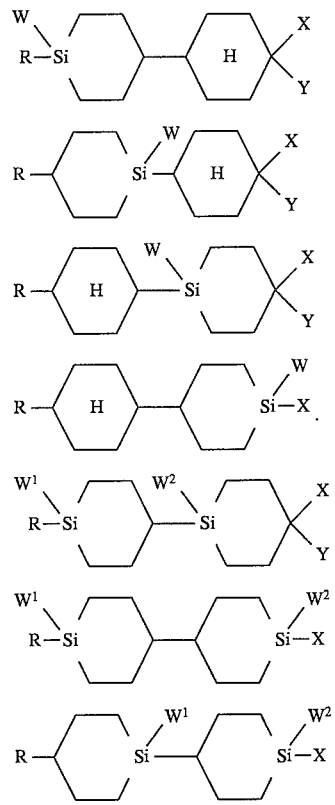

In these formulas, R denotes the following groups listed in (a) through (d):

(a) A linear-chain alkyl group with a carbon number of 1–10, i.e. a methyl, ethyl, n-propyl, n-butyl, n-pentyl, n-hexyl, n-heptyl, n-octyl, n-nonyl or n-decyl group (b) A mono- or di-fluoroalkyl group with a carbon number of 1–10, i.e. fluoromethyl, 1-fluoroethyl, 1-fluoropropyl, 1-fluorobutyl, 1-fluoropentyl, 1-fluorohexyl, 1-fluoroheptyl, 1-fluorooctyl, 1-fluorononyl, 1-fluorodecyl, 2-fluoroethyl, 2-fluoropropyl, 2-fluorobutyl, 2-fluoropentyl, 2-fluorohexyl, 2-fluoroheptyl, 2-fluorooctyl, 2-fluorononyl, 2-fluorodecyl, 3-fluoropropyl, 3-fluorobutyl, 3-fluoropentyl, 3-fluorohexyl, 3-fluoroheptyl, 3-fluorooctyl, 3-fluorononyl, 3-fluorodecyl, 4-fluorobutyl, 4-fluoropentyl, 4-fluorohexyl, 4-fluoroheptyl, 4-fluorooctyl, 4-fluorononyl, 4-fluorodecyl, 5-fluoropentyl, 5-fluorohexyl, 5-fluoroheptyl, 5-fluorooctyl, 5-fluorononyl, 5-fluorodecyl, 6-fluorohexyl, 6-fluoroheptyl, 6-fluorooctyl, 6-fluorononyl, 6-fluorodecyl, 7-fluoroheptyl, 7-fluorooctyl, 7-fluorononyl, 7-fluorodecyl, 8-fluorooctyl, 8-fluorononyl, 8-fluorodecyl, 9-fluorononyl, 9-fluorodecyl, 10-fluorodecyl, difluoromethyl, 1,1-difluoroethyl, 1,1-difluoropropyl, 1,1-difluorobutyl, 1,1-difluoropentyl, 1,1-difluorohexyl, 1,1-difluoroheptyl, 1,1-difluorooctyl, 1,1-difluorononyl, 1,1-difluorodecyl, 2,2-difluoroethyl, 2,2-difluoropropyl, 2,2-difluorobutyl, 2,2-difluoropentyl, 2,2-difluorohexyl, 2,2-difluoroheptyl, 2,2-difluorooctyl, 2,2-difluorononyl, 2,2-difluorodecyl, 3,3-difluoropropyl, 3,3-difluorobutyl, 3,3-difluoropentyl, 3,3-difluorohexyl, 3,3-difluoroheptyl, 3,3-difluorooctyl, 3,3-difluorononyl, 3,3-difluorodecyl, 4,4-difluorobutyl, 4,4-difluoropentyl, 4,4-difluorohexyl, 4,4-difluoroheptyl, 4,4-difluorooctyl, 4,4-difluorononyl, 4,4-difluorodecyl, 5,5-difluoropentyl, 5,5-difluorohexyl, 5,5-difluoroheptyl, 5,5-difluorooctyl, 5,5-difluorononyl, 5,5-difluorodecyl, 6,6-difluorohexyl, 6,6-difluoroheptyl, 6,6-difluorooctyl, 6,6-difluorononyl, 6,6-difluorodecyl, 7,7-difluoroheptyl, 7,7-difluorooctyl, 7,7-difluorononyl, 7,7-difluorodecyl, 8,8-difluorooctyl, 8,8-difluorononyl, 8,8-difluorodecyl, 9,9-difluorononyl or 10,10-difluorodecyl group (c) A branched-chain alkyl group with a carbon number of 3–8, i.e. an isopropyl, sec-butyl, isobutyl, 1-methylbutyl, 2-methylbutyl, 3-methylbutyl, 1-methylpentyl, 2-methylpentyl, 3-methylpentyl, 1-ethylpentyl, 1-methylhexyl, 2-methylhexyl, 3-methylhexyl, 2-ethylhexyl, 3-ethylhexyl, 1-methylheptyl, 2-methylheptyl or 3-methylheptyl group (d) An alkoxyalkyl group with a carbon number of 2–7, i.e. a methoxymethyl, ethoxymethyl, propoxymethyl, butoxymethyl, pentoxymethyl, hexyloxymethyl, methoxyethyl, ethoxyethyl, propoxyethyl, butoxyethyl, pentoxyethyl, methoxypropyl, ethoxypropyl, propoxypropyl, butoxypropyl, methoxybutyl, ethoxybutyl, methoxypentyl, methoxyhexyl or ethoxypentyl group (e) An alkenyl group with a carbon number of 2–8, i.e. a vinyl, 1-propenyl, allyl, 1-butenyl, 3-butenyl, isoprenyl, 1-pentenyl, 3-pentenyl, 4-pentenyl, dimethylallyl, 1-hexenyl, 3-hexenyl, 5-hexenyl, 1-heptenyl, 3-heptenyl, 6-heptenyl or 7-octenyl group W, $W^1$ and $W^2$ independently denote H, F Cl or $CH^{3-}$ X denotes a substitutional group at an equatorial position, specifically CN (only when the ring structure is

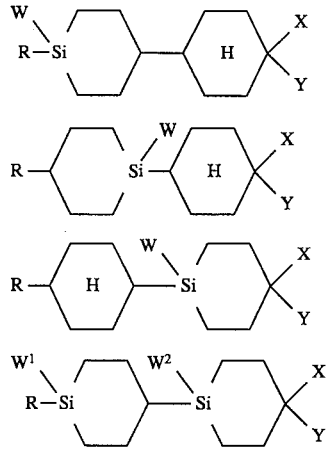

) or one of (f) through (k) shown below: (f) A linear-chain alkyl group with a carbon number of 1–10, i.e. a methyl, ethyl, n-propyl, n-butyl, n-pentyl, n-hexyl, n-heptyl, n-octyl, n-nonyl or n-decyl group (g) An alkyl group with a carbon number of 1–10 whose end group replaced by a trifluoromethyl group, i.e. a trifluoromethyl, trifluoromethylmethyl, trifluoromethylethyl, trifluoromethylpropyl, trifluoromethylbutyl, trifluoromethylpentyl, trifluoromethylhexyl, trifluoromethylheptyl, trifluoromethyloctyl or trifluoromethylnonyl group (h) A linear-chain alkoxy group with a carbon number of 1–10, i.e. a methoxy, ethoxy, n-propoxy, n-butoxy, n-pentoxy, n-hexyloxy, n-heptyloxy, n-octyloxy, n-nonyloxy or n-decyloxy group (i) A linear-chain alkanoyloxy group with a carbon number of 2–10 (only when the ring structure is

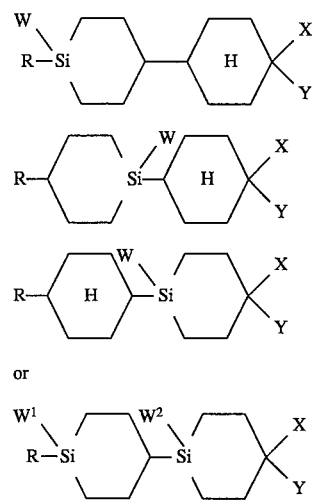

), i.e. an acetoxy, propionyloxy, butylyoxy, pentanoyloxy, hexanoyloxy, heptanoyloxy, octanoyloxy, nonanoyloxy or decanoyloxy group (j) An alkoxycarbonyl group with a carbon number of 1–10, i.e. a methoxycarbonyl, ethoxycarbonyl, propoxycarbonyl, butoxycarbonyl, pentoxycarbonyl, hexyloxycarbonyl, heptyloxycarbonyl, octyloxycarbonyl or nonyloxycarbonyl group (k) An alkoxyalkyl group with a carbon number of 2–7, i.e. a methoxymethyl, ethoxymethyl, propoxymethyl, butoxymethyl, pentoxymethyl, hexyloxymethyl, methoxyethyl, ethoxyethyl, propoxyethyl, butoxyethyl, pentoxyethyl, methoxypropyl, ethoxypropyl, propoxypropyl, butoxypropyl, methoxybutyl, ethoxybutyl, methoxypentyl, methoxyhexyl or ethoxypentyl group Y denotes a substitutional group at an axial position, specifically hydrogen or CN. However, the case in which X and Y are both CN is excluded.

In terms of their ring structures, the compounds of

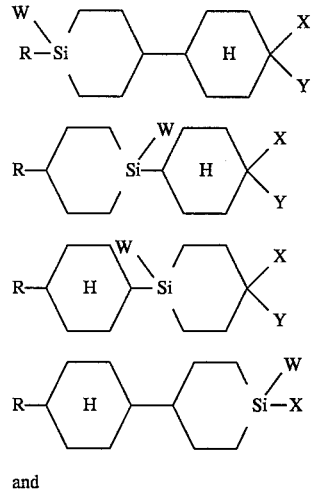

and

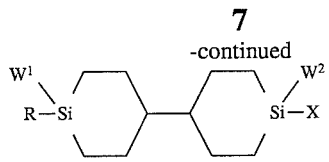

are preferable.

For R, the following groups listed in (l) through (p) are preferable:

(l) A linear-chain alkyl group with a carbon number of 3–7, i.e. a n-propyl, n-butyl, n-pentyl, n-hexyl or n-heptyl group (m) Some mono- or di-fluoroalkyl groups with a carbon number of 1–10 including 2-fluoroethyl, 2-fluoropropyl, 2-fluorobutyl, 2-fluoropentyl, 2-fluorohexyl, 2-fluoroheptyl, 4-fluorobutyl, 4-fluoropentyl, 4-fluorohexyl, 4-fluoroheptyl, 5-fluoropentyl, 5-fluorohexyl, 5-fluoroheptyl, 6-fluorohexyl, 6-fluoroheptyl, 7-fluoroheptyl, 2,2-difluoroethyl, 2,2-difluoropropyl, 2,2-difluorobutyl, 2,2-difluoropentyl, 2,2-difluorohexyl, 2,2-difluoroheptyl, 4,4-difluorobutyl, 4,4-difluoropentyl, 4,4-difluorohexyl, 4,4-difluoroheptyl, 5,5-difluoropentyl, 5,5-difluorohexyl, 5,5-difluoroheptyl, 6,6-difluorohexyl, 6,6-difluoroheptyl and 7,7-difluoroheptyl groups (n) Some branched-chain alkyl groups including isopropyl, 1-methylpropyl, 2-methylpropyl, 1-methylbutyl, 2-methylbutyl, 3-methylbutyl, 1-methylpentyl, 2-methylpentyl and 2-ethylhexyl groups (o) An alkoxyalkyl group with a carbon number of 2–6, i.e. a methoxymethyl, methoxyethyl, methoxypropyl, methoxypentyl, ethoxymethyl, ethoxyethyl, propoxymethyl or pentoxymethyl group (p) Some alkenyl groups including vinyl, 1-propenyl, 3-butenyl, 1-pentenyl, 3-pentenyl, 4-pentenyl, 1-hexenyl, 5-hexenyl, 6-heptenyl and 7-octenyl groups H, F and $CH_3$ groups are desirable for W, $W^1$ and $W^2$.

CN or (q) through (s) shown below is preferable for the substitutional group X at an equatorial position:

(q) A linear-chain alkyl group, an alkyl group with its end group replaced by a trifluoromethyl group or an alkoxy group with a carbon number of 1–5, i.e. a methyl, ethyl, n-propyl, n-butyl, n-pentyl, trifluoromethyl, trifluoromethylmethyl, trifluoromethylethyl, trifluoromethylpropyl, trifluoromethylbutyl, methoxy, ethoxy, n-propoxy, n-butoxy or n-pentoxy group (r) A linear-chain alkanoyloxy or alkoxycarbonyl group with a carbon number of 2–5, i.e. an acetoxy, propionyloxy, butyloxy, pentanoyloxy, methoxycarbonyl, ethoxycarbonyl, propoxycarbonyl or butoxycarbonyl group (s) An alkoxyalkyl group with a carbon number of 2–6, i.e. a methoxymethyl, methoxyethyl, methoxypropyl, methoxypentyl, ethoxymethyl, ethoxyethyl, propoxymethyl or pentoxymethyl group H or CN is preferable for the substitutional group Y at an axial position. However, the case in which X and Y are both CN is excluded.

A manufacturing process of these compounds is described below.

These compounds are prepared by a carbon-carbon bond formation reaction or carbon-silicon bond formation reaction between an organometallic reagent and a compound which has an eliminatable group(s) such as a halogen atom, alkoxy, methanesulfonyl, benzenesulfonyl or p-toluenesulfonyl group. A detailed description is given below.

In the reaction between the organometallic reagent

R—M (M denotes MgP (P denotes a halogen atom), ZnP or Li) and

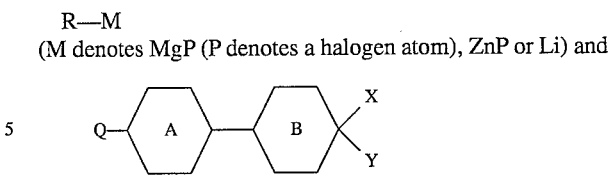

(Q denotes a halogden atom, or an alkoxy, methanesulfonyl, benzenesulfonyl or p-toluenesulfonyl group), when

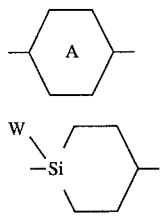

(W denotes H, F, Cl or a $CH_3$ group), Q is a halogen atom or an alkoxy group, for example. Particularly, if Q is a F, Cl or Br atom, or an $OCH_3$ or $OCH_2CH_3$ group, then the carbon-silicon bond formation reaction proceeds easily and gives a high yield of the target product.

Also, when

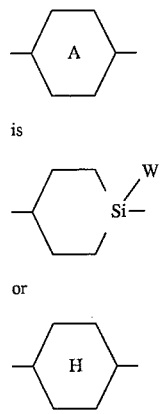

this carbon-carbon bond formation reaction is carried out in the presence of a catalytic amount of copper salt. In this case, Q is a halogen atom or a methanesulfonyl, benzenesulfonyl or p-toluenesulfonyl group, for example. It is particularly preferable if Q is Br or I because then the target product can be obtained with a high yield.

In the reaction between the organometallic reagent

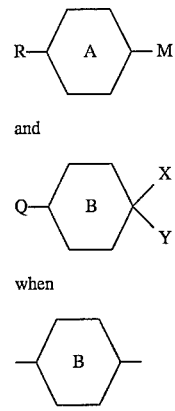

and when is

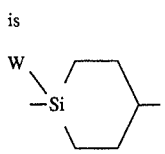

Q is a halogen atom or an alkoxy group, for example. Particularly, if Q is a F, Cl or Br atom, or an $OCH_3$ or $OCH_2CH_3$ group, then the carbon-silicon bond formation reaction proceeds easily and gives a high yield.

Also, when

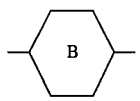

is

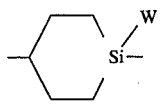

or

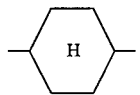

this carbon-carbon bond formation reaction is carried out in the presence of a catalytic amount of copper salt. In this case, Q is a halogen atom or a methanesulfonyl, benzenesulfonyl or p-toluenesulfonyl group, for example. It is particularly preferable if Q is Br or I.

In the reaction between the organometallic reagent

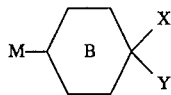

and

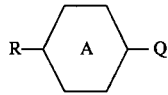

when

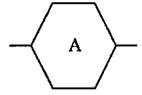

is

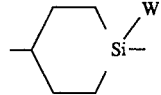

Q is a halogen atom or an alkoxy group, for example. Particularly, if Q is a F, Cl or Br atom, or an $OCH_3$ or $OCH_2CH_3$ group, then the carbon-silicon bond formation reaction proceeds easily and gives a high yield.

When

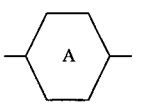

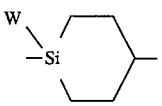

or

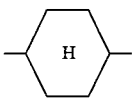

this carbon-carbon bond formation reaction is carried out in the presence of a catalytic amount of copper salt. In this case, Q is a halogen atom or a methanesulfonyl, benzenesulfonyl or p-toluenesulfonyl group, for example. Particularly if Q is Br or I, the target product can be obtained with a high yield.

When the compound produced here is a mixture of trans isomers and cis isomers in terms of the configuration of the silacyclohexane ring, a conventional purification means such as chromatography and recrystallization is employed to separate and purify the trans,trans isomers to obtain the silacyclohexane compound represented by the general formula (I) of this invention.

The silacyclohexane compound of this invention can be mixed with known compounds to obtain a liquid crystal composition. The compound used for mixing to obtain the liquid crystal compound can be chosen from among the known compounds shown below:

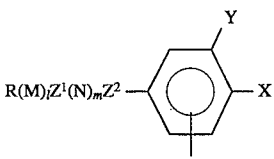

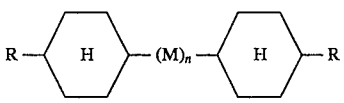

In the above formulas, (M) and (N) denote one of 1) through 5) shown below:
1) A trans-1,4-cyclohexylene group which has no substitution or which has one or more substitutional groups such as F, Cl, Br, CN or alkyl groups
2) A trans-1,4-cyclohexylene group in which O or S is substituted for one or nonadjacent two $CH_2$ groups in the cyclohexane ring
3) A 1,4-cyclohexenylene group
4) A 1,4-phenylene group which has no substitution or which has one or two substitutional groups such as F, Cl, $CH_3$ or CN groups
5) A 1,4-phenylene group in which an N atom is substituted for one or two CH groups in the ring
$Z^1$ and $Z^2$ denote $-CH_2CH_2-$, $-CH=CH-$, $-C\equiv C-$, $-CO_2-$, $-OCO-$, $-CH_2O-$, $-OCH_2-$ or a single bond.
l, m=0, 1 or 2 (where l+m=1, 2 or 3), and n=0, 1 or 2.
R denotes hydrogen, a linear-chain alkyl group with a carbon number of 1–10, a mono- or di-fluoroalkyl group with a carbon number of 1–10, a branched-chain alkyl group with a carbon number of 3–8, an alkoxyalkyl group with a carbon number of 2–7, or an alkenyl group with a carbon number of 2–8.

X denotes CN, F, Cl, $CF_3$, $CF_2Cl$, $CHFCl$, $OCF_3$, $OCHF_2$, $OCF_2Cl$, $OCHFCl$, an alkoxy group, an alkanoyloxy group or a linear-chain alkyl group with a carbon number of 1–10. Y denotes H or F, and Z denotes H or F.

In the above description, if l=2 and n=2, then (M) can contain heterogeneous rings, and if m=2, then (N) can contain heterogeneous rings.

The ratio of one or more types of the silacyclohexane compound of this invention contained in the liquid crystal phase is 1–50 wt %, more preferably 5–30 wt %. The liquid crystal composition can also contain a polygenetic dye(s) to generate a colored guest-host system and additives to change the dielectric anisotropy, viscosity and the orientation of the nematic phase.

The liquid crystal composition thus formed is sealed between transparent plates which have electrodes of desired shapes and is thus used as liquid crystal display elements. This element can have various undercoatings, overcoatings for orientation control, a polarizer plate(s), a filter(s) and a reflector layer(s), as necessary. It can be made into a laminated cell or combined with other display elements. Semiconductor substrates and light sources can also be used to make various types of displays.

For the driving method of the liquid crystal display element, prior-art methods in the industry of liquid crystal display elements, such as the dynamic scattering (DSM) method, the twisted nematic (TN) method, the super twisted nematic (STN) method, the guest-host (GH) method and the polymer dispersion liquid crystal (PDLC) method can be adopted.

EXAMPLE

Example 1

Preparation of trans, trans-4-(4-methoxycyclohexyl)-1-n-propyl-1-silacyclohexane 100 ml of a tetrahydrofuran solution of 1.0M n-propyl magnesium chloride was dripped into a mixture of 23.0 g (93.2 mmol) of 1-chloro-4-(trans-4-methoxycyclohexyl)-1-silacyclohexane and 100 ml of tetrahydrofuran. After a conventional after treatment, the product thus obtained was purified by means of silica-gel column chromatography to obtain 17.1 g (yield 72%) of the trans, trans isomer.

IR vmax: 2928, 2856, 2820, 2098, 1452, 1103, 989, 887, 843 and 820 $cm^{-1}$ (liquid film method) m.p. (melting point): <–60° C., c.p (clearing point): –41° C.

Using the same(process as Example 1, the following compounds of Examples 2–6 were obtained.

Example 2

Trans, trans-4-n-butyl-1-(4-cyanocyclohexyl)-1-methyl-1-silacyclohexane

Example 3

Trans, trans-4-(4-ethoxycyclohexyl)-1-(3-butenyl)-1-silacyclohexane

Example 4

Trans, trans-4-(4-ethoxycyclohexyl)-1-(3-penteny)-1-silacyclohexane

Example 5

Trans, trans-4-(4-n-propyl-4-silacyclohexyl)-1-n-pentyl-1-silacyclohexane

Example 6

Trans, trans-4-[4-(n-pentyloxycarbonyl)silacyclohexyl]-1-n-propyl-1-silacyclohexane

Example 7

Preparation of trans, trans-4-(4-n-propyloxycyclohexyl)-1-n-propyl-1-silacyclohexane 50 ml of a tetrahydrofuran solution of 1.0M 4-propyl-4-silacyclohexyl magnesium bromide was dripped into a mixture of 12.0 g (54.3 mmol) of 4-bromocyclohexyl n-propylether, 100 mg of copper iodide (I), 200 mg of triethyl phosphite and 50 ml of tetrahydrofuran. After a conventional after treatment, the product thus obtained was purified by means of silica-gel column chromatography to obtain 9.60 g (yield 68%) of the trans, trans isomer.

IR vmax: 2929, 2856, 2098, 1452, 1109, 987, 887, 843 and 820 $cm^{-1}$ (liquid film method) m.p. (melting point): –6.3° C., c.p (clearing point): 7.3° C.

Using the same process as Example 7, the following compounds of Examples 8–12 were obtained.

Example 8

Trans, trans-1-n-butyl-4-(4-cyanocyclohexyl)-1-silacyclohexane

Example 9

Trans, trans-4-(4-cyanocyclohexyl)-1-n-pentyl-1-silacyclohexane

Example 10

Trans, trans-4-(4-hexanoyloxycyclohexyl)-1-n-propyl-1-silacyclohexane

Example 11

Trans, trans-1-fluoro-4-(4-n-propyloxycyclohexyl)-1-n-propyl-1-silacyclohexane

Example 12

Trans-1-n-pentyl-4-(gamma-4-cyano-trans-4-n-propylcyclohexyl)-1-silacyclohexane

Example 13

Preparation of trans, trans-4-(4-methoxycyclohexyl)-1-n-pentyl-1-silacyclohexane 50 ml of a tetrahydrofuran solution of 2.0M 4-methoxyclohexyl magnesium bromide was dripped into a mixture of 28.0 g (94.5 mmol) of 4-iodo-1-n-pentyl-1-silacyclohexane, 100 mg of copper chloride (I) and 80 ml of tetrahydrofuran. After a conventional after treatment, the product thus obtained was purified by means of silica-gel column chromatography to obtain 18.9 g (yield 7.1%) of the trans, trans isomer.

Using the same process as Example 13, the following compounds of Examples 14–17 were obtained.

Example 14

Trans, trans-1-methoxymethyl-4-(4-n-propylcyclohexyl)-1-silacyclohexane

Example 15

Trans, trans-1-isopentyl-4-(4-methoxycyclohexyl)-1-silacyclohexane

Example 16

Trans, trans-4-[4-(3,3,3-trifluoropropyl)cyclohexyl]-1-n-propyl-1-silacyclohexane Example 17

Trans, trans-4-[4-(3-methoxypropyl)cyclohexyl]-1-n-pentyl-1-silacyclohexane

Example 18

An example of the liquid crystal compositions

A liquid crystal composition comprising 25 wt % of 4-(trans-4-n-ethylcyclohexyl)-3',4'-difluorobiphenyl, 25 wt % of 4-(trans-4-n-propylcyclohexyl)-3',4'-difluorobiphenyl and 50 wt % of 4-(trans-4-n-pentylcyclohexyl)-3',4'-difluorobiphenyl exhibits a viscosity at 20° C. of 32.5 mPa.s and an anisotropy of the refractive index of 0.1405.

A liquid crystal mixture comprising 85 wt % of the mixture described above and 15 wt % of trans, trans-4-(4-propyloxycyclohexyl)-1-n-propyl-1-silacyclohexane obtained in Example 4 exhibits a viscosity at 20° C. of 27.5 mPa.s and an anisotropy of the refractive index at 25° C. of 0.1230.

As described thus far, this invention can provide silacyclohexane compounds with a Si atoms(s) as a silacyclohexane ring composing element. These silacyclohexane compounds have an effect of reducing the anisotropy of the refractive index and the viscosity, and therefore a liquid crystal element using a liquid crystal composition containing these compounds can have a wider angle of visibility and a faster response time. Also, for those for which Y is CN in the general formula (I), the dielectric anisotropy becomes negative.

We claim:

1. A silacyclohexane compound represented by the following general formula (I):

 (I)
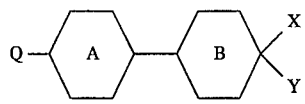

wherein R denotes a linear-chain alkyl group with a carbon number of 1–10, a mono- or di-fluoroalkyl group with a carbon number of 1–10, a branched-chain alkyl group with a carbon number of 3–8, an alkoxyalkyl group with a carbon number of 2–7, or an alkenyl group with a carbon number of 2–8:

at least one of

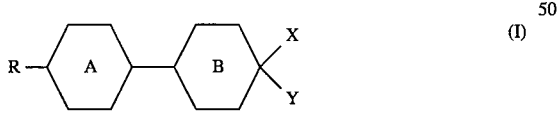

denotes a 1-sila-1,4-cyclohexylene or a 4-sila-1,4-cyclohexylene group whose silicon at position 1 or position 4 has a substitutional group of H, F, Cl or CH$_3$, and the other denotes a 1,4-cyclohexylene group, a 1-sila-1,4-cyclohexylene or a 4-sila-1,4-cyclohexylene group whose silicon at position 1 or 4 has a substitutional group of H, F, Cl or CH$_3$;

X denotes a substitutional group at an equatorial position, specifically CN, an alkyl group with a carbon number of 1–10 and with its end group replaced by a trifluoromethyl group, an alkoxy group with a carbon number of 1–10, an alkanoyloxy group with a carbon number of 2–10, an alkoxycarbonyl group with a carbon number of 1–10, a linear-chain alkyl group with a carbon number of 1–10, or an alkoxyalkyl group with a carbon number of 2–7;

Y denotes a substitutional group at an axial position, specifically H or CN when Y is connected to a carbon atom in said (B) group or H, F, Cl or CH$_3$ when Y is connected to a silicon atom in said (B) group; and the relationship between R and said (B) group as well as between said (A) group and the substitutional group X is trans.

2. A method of preparing the silacyclohexane compound as described in claim 1 characterized by the use of a carbon-carbon bond formation reaction or a carbon-silicon bond formation reaction between an organometallic reagent

R—M (M denotes MgP (P denotes a halogen atom), ZnP or Li) and

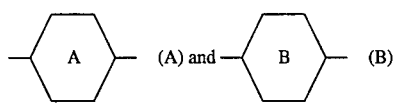

(Q denotes a halogen atom, or an alkoxy, methanesulfonyl, benzenesulfonyl or p-toluenesulfonyl group).

3. A method of preparing the silacyclohexane compound as described in claim 1 characterized by the use of a carbon-carbon bond formation reaction or a carbon-silicon bond formation reaction between an organometallic reagent

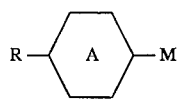

and

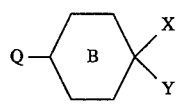

wherein M denotes MgP (P denotes halogen), ZnP or Li and Q denotes a halogen, alkoxy, methanesulfonyl, benzene sulfonyl or p-toluenesulfonyl group.

4. A method of preparing the silacyclohexane compound as described in claim 1 characterized by the use of a carbon-carbon bond formation reaction or a carbon-silicon bond formation reaction between an organometallic reagent

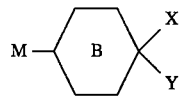

and

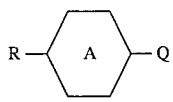
wherein M detones MgP (P denotes halogen) ZnP or Li and Q denotes a halogen, alkoxy, methanesulfonyl, benzenesulfonyl or p-toluene sulfonyl group.
5. A liquid crystal composition comprising the silacyclohexane compound as described in claim 1.
6. A liquid crystal display element comprising the liquid crystal composition as described in claim 5.
* * * * *